US012232755B2

(12) United States Patent
Phan et al.

(10) Patent No.: US 12,232,755 B2
(45) Date of Patent: Feb. 25, 2025

(54) LESION CROSSING SHOCK WAVE CATHETER

(71) Applicant: Shockwave Medical, Inc., Santa Clara, CA (US)

(72) Inventors: Huy Phan, Santa Clara, CA (US); Hoa Nguyen, Santa Clara, CA (US); Chi Long, Santa Clara, CA (US); Todd Jenkins, Santa Clara, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 479 days.

(21) Appl. No.: 17/537,325

(22) Filed: Nov. 29, 2021

(65) Prior Publication Data

US 2022/0183708 A1 Jun. 16, 2022

Related U.S. Application Data

(60) Provisional application No. 63/124,639, filed on Dec. 11, 2020.

(51) Int. Cl.
*A61B 17/225* (2006.01)
*A61B 17/22* (2006.01)

(52) U.S. Cl.
CPC .. *A61B 17/225* (2013.01); *A61B 2017/22045* (2013.01); *A61B 2017/22048* (2013.01);
(Continued)

(58) Field of Classification Search
CPC ............ A61B 17/225; A61B 17/12031; A61B 17/12036; A61B 17/12109;
(Continued)

(56) References Cited

U.S. PATENT DOCUMENTS 3,412,288 A 11/1968 Ostrander
3,413,976 A 12/1968 Voolfovich
(Continued)

FOREIGN PATENT DOCUMENTS

AU 2009313507 B2 11/2014
AU 2013284490 B2 5/2018
(Continued)

OTHER PUBLICATIONS

Advisory Action received for U.S. Appl. No. 17/021,905, mailed on Nov. 22, 2022, 4 pages.
(Continued)

*Primary Examiner* — Brigid K Byrd
(74) *Attorney, Agent, or Firm* — Morrison & Foerster LLP

(57) ABSTRACT

The present invention provides a catheter for treating occlusions in blood vessels. An exemplary catheter for treating occlusions in blood vessels comprises a tubular inner member including a base segment with a first lumen defining a fluid inlet port, and a second lumen defining a fluid outlet port. An extension segment is distal to the base segment. The extension segment has a reduced cross-section. An emitter assembly includes a first insulated wire extending through the second lumen and a second insulated wire, and a conductive sheath wrapped circumferentially around the first insulated wire, the second insulated wire, and the extension segment. A cap or balloon is sealably attached to the distal end of the catheter and surrounds the emitter assembly, said cap or balloon being fillable with conductive fluid.

10 Claims, 11 Drawing Sheets

(52) U.S. Cl.
CPC ............... *A61B 2017/22062* (2013.01); *A61B 2017/22067* (2013.01)

(58) Field of Classification Search
CPC ........... A61B 2017/22001; A61B 2017/22007; A61B 2017/22045; A61B 2017/22048; A61B 2017/22062; A61B 2017/22067; A61B 2017/22021; A61B 2017/22025; A61B 2017/22038; A61B 2017/22051; A61B 2017/22079; A61B 2017/22094; A61B 2017/22091; A61B 17/22022; A61B 17/12136

See application file for complete search history.

(56) References Cited

U.S. PATENT DOCUMENTS

| | | |
|---|---|---|
| 3,785,382 A | 1/1974 | Schmidt et al. |
| 3,902,499 A | 9/1975 | Shene |
| 4,027,674 A | 6/1977 | Tessler et al. |
| 4,030,505 A | 6/1977 | Tessler |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemeison |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,231,976 A | 8/1993 | Wiksell |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,321,715 A | 6/1994 | Trost |
| 5,324,255 A | 6/1994 | Passafaro |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,431,173 A | 7/1995 | Chin et al. |
| 5,472,406 A | 12/1995 | De La Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | De La Torre et al. |
| 5,846,218 A | 12/1998 | Brisken et al. |
| 5,893,840 A | 4/1999 | Hull et al. |
| 5,931,805 A | 8/1999 | Brisken |
| 6,007,530 A | 12/1999 | Domhofer et al. |
| 6,024,718 A | 2/2000 | Chen et al. |
| 6,033,371 A | 3/2000 | Torre et al. |
| 6,080,119 A | 6/2000 | Schwarze et al. |
| 6,083,232 A | 7/2000 | Cox |
| 6,113,560 A | 9/2000 | Simnacher |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,124 B1 | 8/2002 | Esch et al. |
| 6,514,203 B2 | 2/2003 | Bukshpan |
| 6,524,251 B2 | 2/2003 | Rabiner et al. |
| 6,589,253 B1 | 7/2003 | Comish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,241,295 B2 | 7/2007 | Maguire |
| 7,505,812 B1 | 3/2009 | Eggers et al. |
| 7,569,032 B2 | 8/2009 | Naimark et al. |
| 7,873,404 B1 | 1/2011 | Patton |
| 7,951,111 B2 | 5/2011 | Drasler et al. |
| 8,162,859 B2 | 4/2012 | Schultheiss |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins |
| 8,956,374 B2 | 2/2015 | Hawkins |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,730,715 B2 | 8/2017 | Adams |
| 9,993,292 B2 | 6/2018 | Adams et al. |
| 10,039,561 B2 | 8/2018 | Adams et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,602,363 B2 | 3/2023 | Nguyen |
| 11,622,780 B2 | 4/2023 | Nguyen et al. |
| 11,696,799 B2 | 7/2023 | Adams et al. |
| 11,771,449 B2 | 10/2023 | Adams et al. |
| 11,950,793 B2 | 4/2024 | Nguyen |
| 2001/0044596 A1 | 11/2001 | Jaafar |
| 2002/0045890 A1 | 4/2002 | Celliers et al. |

(56) References Cited

U.S. PATENT DOCUMENTS

| | | |
|---|---|---|
| 2002/0077643 A1* | 6/2002 | Rabiner ............... A61N 7/022 606/169 |
| 2002/0177889 A1 | 11/2002 | Brisken et al. |
| 2003/0004434 A1 | 1/2003 | Greco et al. |
| 2003/0060813 A1 | 3/2003 | Loeb et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0240146 A1* | 10/2005 | Nash ............... A61B 17/32037 604/35 |
| 2005/0245866 A1 | 11/2005 | Azizi |
| 2005/0251131 A1 | 11/2005 | Lesh |
| 2006/0004286 A1 | 1/2006 | Chang et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1* | 7/2007 | Kovalcheck ........... A61B 18/14 606/39 |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2008/0294037 A1 | 11/2008 | Richter |
| 2009/0041833 A1 | 2/2009 | Bettinger et al. |
| 2009/0227992 A1 | 9/2009 | Nir et al. |
| 2009/0234282 A1 | 9/2009 | McAndrew et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2009/0312768 A1 | 12/2009 | Hawkins et al. |
| 2010/0016862 A1 | 1/2010 | Hawkins et al. |
| 2010/0022950 A1* | 1/2010 | Anderson ........... A61B 1/00114 604/100.01 |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0125244 A1 | 5/2010 | McAndrew |
| 2010/0274189 A1 | 10/2010 | Kurth et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0203255 A1 | 8/2012 | Hawkins et al. |
| 2012/0221013 A1 | 8/2012 | Hawkins et al. |
| 2012/0271339 A1 | 10/2012 | O'Beirne et al. |
| 2012/0289889 A1* | 11/2012 | Genstler ........... A61B 17/2202 604/22 |
| 2013/0030431 A1 | 1/2013 | Adams |
| 2013/0030447 A1 | 1/2013 | Adams |
| 2013/0041355 A1 | 2/2013 | Heeren et al. |
| 2014/0005576 A1 | 1/2014 | Adams et al. |
| 2014/0039513 A1* | 2/2014 | Hakala ............... A61B 17/22022 606/128 |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0243820 A1 | 8/2014 | Adams |
| 2014/0243847 A1 | 8/2014 | Hakala et al. |
| 2014/0288570 A1 | 9/2014 | Adams |
| 2014/0350401 A1 | 11/2014 | Sinelnikov |
| 2015/0073430 A1 | 3/2015 | Hakala et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0135828 A1* | 5/2016 | Hawkins ........... A61B 17/22012 606/128 |
| 2016/0151081 A1 | 6/2016 | Adams et al. |
| 2016/0174995 A1 | 6/2016 | Turjman et al. |
| 2016/0183957 A1 | 6/2016 | Hakala et al. |
| 2016/0324534 A1 | 11/2016 | Hawkins et al. |
| 2017/0135709 A1 | 5/2017 | Nguyen et al. |
| 2017/0151415 A1 | 6/2017 | Maeda et al. |
| 2017/0311965 A1 | 11/2017 | Adams |
| 2018/0098779 A1 | 4/2018 | Betelia et al. |
| 2018/0360482 A1 | 12/2018 | Nguyen |
| 2019/0150960 A1 | 5/2019 | Nguyen et al. |
| 2019/0365400 A1 | 12/2019 | Adams et al. |
| 2021/0085347 A1 | 3/2021 | Phan et al. |
| 2021/0085383 A1 | 3/2021 | Vo et al. |
| 2021/0177445 A1 | 6/2021 | Nguyen |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0190316 A1 | 6/2023 | Nguyen |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2024/0268842 A1 | 8/2024 | Phan et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 103068330 A | 4/2013 |
| CN | 203564304 U | 4/2014 |
| CN | 104582621 A | 4/2015 |
| CN | 104736073 A | 6/2015 |
| CN | 105188848 A | 12/2015 |
| CN | 107072666 A | 8/2017 |
| CN | 109674508 A | 4/2019 |
| CN | 111067591 A | 4/2020 |
| DE | 3038445 A1 | 5/1982 |
| DE | 202006014285 U1 | 12/2006 |
| EP | 442199 A2 | 8/1991 |
| EP | 571306 A1 | 11/1993 |
| EP | 623360 A1 | 11/1994 |
| EP | 647435 A1 | 4/1995 |
| EP | 1596746 A2 | 11/2005 |
| EP | 2253884 A1 | 11/2010 |
| EP | 2362798 B1 | 4/2014 |
| EP | 3434209 A1 | 1/2019 |
| EP | 3473195 A1 | 4/2019 |
| JP | 60-191353 U | 12/1985 |
| JP | S61135648 A | 6/1986 |
| JP | 62-099210 U | 6/1987 |

(56) References Cited

FOREIGN PATENT DOCUMENTS

| | | | |
|---|---|---|---|
| JP | 62-275446 A | 11/1987 |
| JP | 3-63059 A | 3/1991 |
| JP | 6-125915 A | 5/1994 |
| JP | H06-125915 A | 5/1994 |
| JP | 7-47135 A | 2/1995 |
| JP | 8-89511 A | 4/1996 |
| JP | H10-99444 A | 4/1998 |
| JP | 10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2014208305 A | 11/2014 |
| JP | 2015525657 A | 9/2015 |
| JP | 2015528327 A | 9/2015 |
| JP | 6029828 B2 | 11/2016 |
| JP | 6081510 B2 | 2/2017 |
| JP | 2020524032 A | 8/2020 |
| WO | WO-1989011307 A1 | 11/1989 |
| WO | WO-1992003975 A1 | 3/1992 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010014515 A3 | 8/2010 |
| WO | WO-2010054048 A3 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2013169807 A1 | 11/2013 |
| WO | WO-2014025397 A1 | 2/2014 |
| WO | WO-2014025620 A1 | 2/2014 |
| WO | WO-2015017499 A1 | 2/2015 |
| WO | WO-2016077627 A1 | 5/2016 |
| WO | WO-2016109739 A1 | 7/2016 |
| WO | WO-2019099218 A1 | 5/2019 |

OTHER PUBLICATIONS

Final Office Action received for U.S. Appl. No. 17/021,905, mailed on Sep. 12, 2022, 11 pages.
Non-Final Office Action received for U.S. Appl. No. 17/021,905, mailed on Apr. 8, 2022, 11 pages.
Notice of Allowance received for U.S. Appl. No. 17/185,276, mailed on Jan. 4, 2023, 8 pages.
Notice of Allowance received for U.S. Appl. No. 17/185,276, mailed on Oct. 26, 2022, 10 pages.
Office Action received for Chinese Patent Application No. 201880040835.6, mailed on Oct. 14, 2022, 8 pages.
Requirement for Restriction/Election received for U.S. Appl. No. 17/021,905 mailed on Nov. 8, 2021, 5 pages.
Advisory Action received for U.S. Appl. No. 13/615,107, mailed on Nov. 6, 2015, 3 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Advisory Action Received for U.S. Appl. No. 12/581,295, mailed on Jul. 3, 2014, 3 pages.
Advisory Action Received for U.S. Appl. No. 13/049,199, mailed on Jun. 7, 2012, 3 pages.
Advisory Action received for U.S. Appl. No. 13/267,383, mailed on Jan. 6, 2014, 4 pages.
Decision of Appeals Notice received for Japanese Patent Application No. 2011-534914, mailed on Oct. 17, 2016, 2 pages of Official Copy only.
Decision to Grant received for European Patent Application No. 13756766.5, mailed on May 27, 2016, 2 pages.
Decision to Grant received for European Patent Application No. 09825393.3, mailed on Mar. 13, 2014, 2 pages.
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.
Extended European Search Report received for European Patent Application No. 13827971.6, mailed on Apr. 12, 2016, 8 pages.
Extended European Search Report received for European Patent Application No. 21191690.3, mailed on Jan. 17, 2022, 3 pages.
Final Office Action received for U.S. Appl. No. 12/482,995, mailed on Jul. 22, 2011, 14 pages.
Final Office Action received for U.S. Appl. No. 12/501,619, mailed on Feb. 21, 2012, 12 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 13/049,199, mailed on Apr. 4, 2012, 10 pages.
Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013, 7 pages.
Final Office Action Received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107 mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 14/273,063, mailed on Dec. 28, 2016, 11 pages.

(56) References Cited

OTHER PUBLICATIONS

Final Office Action received for U.S. Appl. No. 14/660,539, mailed on Aug. 3, 2017, 11 pages.
Intention to Grant received for European Patent Application No. 13756766.5, mailed on Jan. 8, 2016, 5 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Preliminary Report on Patentability received for PCT Patent Application No. PCT/US2015/029088, mailed on Nov. 17, 2016, 8 pages.
International Search Report and Written Opinion Received for PCT Application No. PCT/US2018/034855, mailed on Aug. 23, 2018, 13 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2020/050899 mailed on Feb. 2, 2021, 19 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.
International Search Report and Written Opinion received for PCT Patent Application No. PCT/US2021/062666 mailed on Mar. 25, 2022, 9 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.
Invitation to Pay Additional Fees for PCT Patent Application No. PCT/US2020/050899, mailed on Nov. 5, 2020, 16 pages.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non Final Office Action received for U.S. Appl. No. 13/049,199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/615,107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Mar. 6, 2017, 14 pages.
Non-Final Office Action received for U.S. Appl. No. 14/660,539, mailed on Nov. 24, 2017, 10 pages.

(56) References Cited

OTHER PUBLICATIONS

Non-Final Office Action received for U.S. Appl. No. 14/693,155, mailed on Jan. 15, 2016, 6 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Japanese Patent Application No. 2015-036444, mailed on Jan. 13, 2017, 3 pages (Official Copy Only).
Notice of Allowance received for U.S. Appl. No. 12/482,995, mailed on Dec. 24, 2014, 6 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/049,199, mailed on Jan. 13, 2015, 4 pages.
Notice of Allowance received for U.S. Appl. No. 13/049,199, mailed on Dec. 15, 2014, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/615,107, mailed on Dec. 31, 2015, 10 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 13/957,276, mailed on Aug. 28, 2015, 9 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,276, mailed on Feb. 25, 2015, 8 pages.
Notice of Allowance received for U.S. Appl. No. 14/271,342, mailed on Mar. 13, 2015, 5 pages.
Notice of Allowance received for U.S. Appl. No. 14/273,063, mailed on Apr. 12, 2017, 7 pages.
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Canadian Patent Application No. 2,727,429, mailed on Apr. 14, 2015, 4 pages.

Office Action received for Canadian Patent Application No. 2,779,600, mailed on Jan. 4, 2016, 6 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016, 9 pages (3 pages of English translation and 6 pages of Official copy).
Office Action received for Chinese Patent Application No. 201380041656.1, mailed on Jul. 5, 2016, 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for European Patent Application No. 09763640.1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation).
Office Action Received for Japanese Patent Application No. 2011-534914, mailed on Jan. 13, 2015, 9 pages (7 pages of English Translation and 2 pages of Official Copy).
Office Action received for Japanese Patent Application No. 2011-534914, mailed on May 10, 2016, 10 pages (4 pages of Official Copy and 6 pages of English Translation).
Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017, 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2016-143049, mailed on Apr. 24, 2017, 5 pages (2 pages of English Translation and 3 pages of Official copy).
Office Action received for Japanese Patent Application No. 2019-569918, mailed on Feb. 14, 2022, 6 pages.
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Rosenschein et al., (1992). "Shock-Wave Thrombus Ablation, a New Method for Noninvasive Mechanical Thrombolysis," The American Journal of Cardiology, 70:1358-1361.
Third Party Preissuance Submission for U.S. Appl. No. 15/989,016, filed Mar. 8, 2019, 3 pages.
Zhong et al., (1997). "Transient Oscillation of Cavitation Bubbles Near Stone Surface During Electrohydraulic Lithotripsy," Journal of Endourology, 11:55-61.

\* cited by examiner

LESION CROSSING SHOCK WAVE CATHETER

PRIORITY

This application claims priority to U.S. Provisional Patent Application Ser. No. 63/124,639, filed Dec. 11, 2020.

FIELD OF THE DISCLOSURE

The present disclosure relates generally to catheter devices that can be used to cross a calcified lesion. The catheter includes a distal shock wave generator configured with a very low profile to permit advancement through narrow vascular structures.

BACKGROUND

A wide variety of catheters have been developed to treat arterial disease. For example, treatment systems for percutaneous coronary angioplasty or peripheral angioplasty use angioplasty balloons to dilate a lesion (e.g., a calcified lesion) and restore normal blood flow in an artery. In these types of procedures, a catheter carrying a balloon is advanced into the vasculature along a guidewire until the balloon is aligned with calcified plaques. The balloon is then pressurized to reduce or break the calcified plaques and push them back into the vessel wall. The balloon can have smooth walls or be provided with structures that physically score the lesions in the vessel. Other catheters, known as atherectomy devices, have rotating members for drilling out the lesion.

More recently, catheters have been developed that include one or more electrode pairs positioned inside an angioplasty balloon. In these devices, the catheter is advanced over a guidewire in a patient's vasculature until it is proximal to a lesion. The balloon is inflated with conductive fluid to contact the lesion and then shock wave generators are fired to produce shock waves that direct acoustic waves into the lesion. Shock wave devices are particularly effective for treating calcified lesions because the acoustic waves can crack the lesions without harming the surrounding vasculature. Once the lesions are cracked, the balloon can be expanded further in the vessel to create an improved blood flow lumen.

The shock wave generators are typically electrode pairs excited by the application of high voltage pulses. Efforts have been made to reduce the size of the electrode pairs to allow access to tighter and harder-to-cross calcified lesions. Examples of such low profile designs can be found in U.S. Pat. Nos. 8,747,416 and 10,555,744, and U.S. Publication Nos. 2018/0360482 and 2019/0150960, all of which are incorporated herein by reference.

While the low profile designs discussed above have been deployed in both coronary and peripheral vessel applications, even those designs have difficulty crossing a partial or total occlusion in vasculature. One approach to deal with the problem is to use guidewire having a shock wave generator at the distal tip. In that case, the catheter proximal and distal shaft portions are reinforced to support the advancement of the guidewire into the occlusion. One or more shock waves are generated to partially open the blockage. The guidewire can then be advanced further into the occlusion where additional shock waves are generated. This sequence can be continued in order to move the guidewire through the occlusion and provide a large enough channel that a balloon catheter can now be inserted. An example of such a shock wave guidewire design can be found in U.S. Pat. No. 9,730,715, incorporated herein by reference.

While placing a shock wave electrode on the tip of a guidewire can lead to an extremely low profile structure, such an approach has some disadvantages compared to low profile designs that include an inflatable balloon. For example, the guidewire necessarily has a soft tip which cannot be easily pushed through a blockage. In addition, the guidewire design is unipolar, with one electrode at the tip of the guidewire and the second electrode defined by a pad affixed to the patient's body. This means that the patient is part of the electrical circuit. In addition, the guidewire design does not have a balloon at the tip. A balloon is advantageous in that it can shield the tissue from direct contact with the plasma that is generated during shock wave creation. A balloon also ensures that the conductive fluid surrounds the electrodes during shock wave generation.

Accordingly, there is a need to provide a catheter design with a lower profile than previous approaches that incorporates a low-profile cap or a low-profile angioplasty balloon and includes a bipolar electrical circuit to generate shockwaves inside the cap or the balloon.

BRIEF SUMMARY

The above objects are realized in a catheter for treating occlusions in blood vessels that has at least one electrode pair inside a low-profile cap or angioplasty balloon at the distal end of the catheter. In some designs, the electrodes are coplanar reducing the diameter of the device. In addition, a low-profile cap or balloon that does not need to be folded before insertion into the cardiovascular system is used. Such a cap or balloon can be expanded a relatively small amount sufficient to immerse the electrodes in a conductive fluid before generating shock waves at the electrodes to treat an occlusion. The cap or balloon can be made of material having elastomeric properties such that it returns to its original low profile configuration when it is deflated following treatment.

An exemplary catheter for treating occlusions in blood vessels comprises: a tubular inner member comprising: a base segment defining: a first lumen defining a fluid inlet port, and a second lumen defining a fluid outlet port; an extension segment distal to the base segment, wherein the extension segment has a reduced cross-section than the base segment; an emitter assembly comprising: a first insulated wire extending through the second lumen, a second insulated wire, and a conductive sheath wrapped circumferentially around the first insulated wire, the second insulated wire, and the extension segment, and a cap or balloon sealably attached to the distal end of the catheter and surrounding the emitter assembly, said cap or balloon being fillable with conductive fluid.

In some embodiments, the extension segment is configured to receive a guidewire.

In some embodiments, the extension segment is connected to a third lumen within the base segment, and wherein the extension segment is formed by removing walls of the first lumen and the second lumen at the distal end of the inner member.

In some embodiments, the fluid inlet port comprises a tubing extending from the first lumen.

In some embodiments, the second wire extends through the first lumen.

In some embodiments, the distal end of the first lumen is sealed to expose only a portion of the second wire and a portion of the tubing.

In some embodiments, the conductive fluid is configured to flow around the conductive sheath and exit via a crack formed by the outside of the conductive sheath and the second lumen.

In some embodiments, the emitter assembly comprises: a first electrode pair comprising the conductive sheath and a conductive distal end of the first insulated wire spaced apart from the conductive sheath; and a second electrode pair comprising the conductive sheath and a conductive distal end of the second insulated wire spaced apart from the conductive sheath.

In some embodiments, the first electrode pair and the second electrode pair are located approximately 180 degrees apart circumferentially around the conductive sheath.

In some embodiments, the proximal ends of the first wire and the second wire are connectable to a pulsed voltage source.

In some embodiments, the catheter further comprises: a reinforced wire sheath wrapped circumferentially around the inner member sheath.

In some embodiments, the reinforced wire sheath comprises at least one braided or coiled metal wire encapsulated in a polymer.

In some embodiments, the cap or balloon is flexible and can be expanded by inflation with the conductive fluid and wherein the maximum inflated diameter of the flexible cap or balloon is no more than 15% greater than the deflated diameter of the flexible cap.

In some embodiments, the cap or balloon is made of material having elastomeric properties such that, after being inflated, the cap or balloon returns to a low profile configuration when deflated.

In some embodiments, the cap comprises an extruded polymer tube.

In some embodiments, when the balloon is in a deflated state, a surface area of the balloon is small enough that the balloon is not folded when the catheter is advanced into a blood vessel.

In some embodiments, the first wire and the second wire are flattened.

In some embodiments, the first wire or the second wire comprises at least one of copper and stainless steel.

In some embodiments, the conductive sheath of oval-shaped.

In some embodiments, the catheter further comprises a soft tip that tapers toward the distal end of the catheter.

In some embodiments the catheter includes a tubular inner member having a proximal portion with a first diameter and a distal end portion having a second diameter smaller than the first diameter, with the proximal portion of the inner member including four circumferentially positioned flutes, each flute receiving one of four tubes. A first wire is located in a first tube and extends distally beyond the first tube. A second wire is located in a second tube and extends distally beyond the second tube. A third tube is connectable to a source of conductive fluid and a fourth tube is configured to define a return patent for the conductive fluid. A cylindrical insulation sheath is positioned around the distal portion of the inner member and radially inside the distal ends of the first and second wires. A cylindrical conductive sheath surrounds the distal ends of the first and second wires and defines two electrode pairs. A sheath surrounds the proximal portion of the inner member. A flexible cap surrounds the conductive sheath and the distal tip of the catheter.

DETAILED DESCRIPTION

Figure 1:
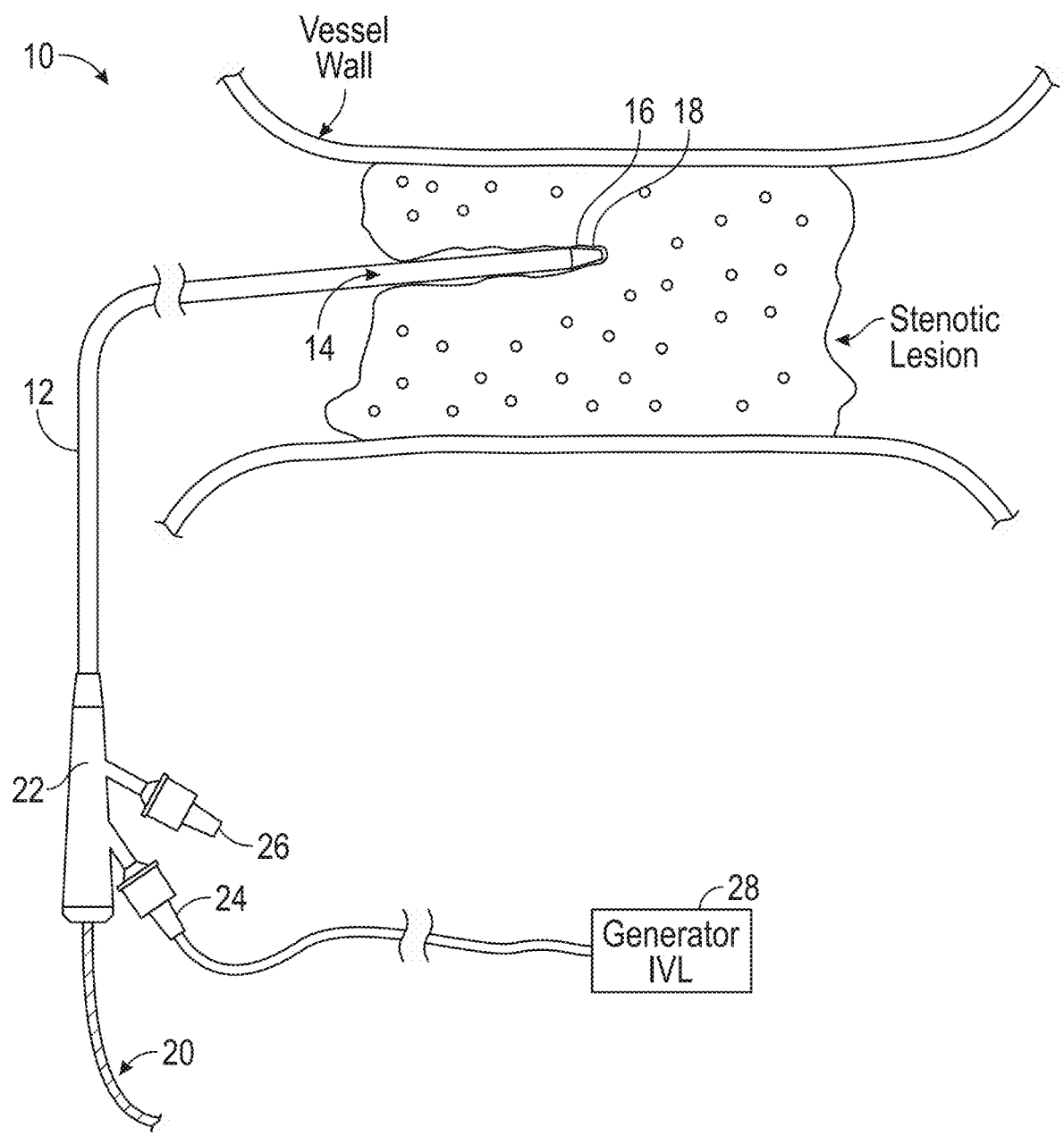
FIG. 1 is an illustration of a shock wave angioplasty catheter being used to treat an occlusion in a blood vessel, in accordance with some embodiments of the subject invention.

The following description is presented to enable a person of ordinary skill in the art to make and use the various embodiments disclosed herein. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

The assignee herein has developed a number of low-profile shock wave electrodes that may be suitable for use in angioplasty and/or valvuloplasty procedures. For example, in U.S. Pub. No. 2019/0150960, the assignee discloses a low-profile electrode assembly, in which an outer electrode is formed by a conductive sheath, and an inner electrode is formed by removing a portion of an insulated wire (e.g., cutting a hole in the insulating layer near the end of the wire) to expose an electrically conductive portion of the insulated wire. The inner electrode is placed a controlled distance apart from the side edge of the conductive sheath to allow for a reproducible arc for a given current and voltage.

More recently, the assignee has developed a number of coplanar electrode assemblies for use in shock wave catheters. These designs provide novel configurations of electrode pairs having, e.g., helical structures and tongue-and-groove designs, with respective electrodes on the same lateral plane to limit the overall thickness of the electrode assemblies. These assemblies are particularly advantageous for generating shock waves in tight, hard-to-pass lesions or totally occluded vasculature. For example, in U.S. Pat. No. 9,993,292 and U.S. Publication No. 2018/0098779, incorporated herein by reference, the assignee discloses forming electrode pairs from helically wound wires to generate shock waves at various gaps positioned circumferentially around a tubular structure. In U.S. Pat. No. 10,555,744, also incorporated herein by reference, the assignee discloses a tongue-and-groove electrode assembly in which electrode pairs are formed from a groove-shaped cut-out in a conductive sheath and a coplanar tongue-shaped protrusion extending into the groove-shaped cut-out.

Described herein are catheters incorporating low-profile design elements that permit intravascular lithotripsy (IVL) treatment in tighter, hard-to-cross calcific lesions and coronary total occlusions. The present invention is similar to existing IVL systems in that it can comprise an array of lithotripsy emitters (e.g., electrode pairs) on a catheter that is entered into a patient's vasculature to deliver shock waves to an occlusion. However, the present invention additionally includes an inner member with a reduced distal segment for providing a low-profile distal end. One or more emitter assemblies can be installed around the reduced distal segment.

In some embodiments, the catheters described herein include a low-profile cap or angioplasty balloon attached to the distal end of the catheter that can be positioned in a patient's vasculature without folding. The low profile of the no-fold cap or balloon advantageously allows the catheter to advance into even tighter regions of vasculature, such as those that are partially or totally occluded. Once the balloon has been positioned, the elastomeric material properties of the low-profile cap or balloon allow the balloon to inflate with conductive fluid to increase the balloon's profile, i.e., in order to contact an occlusion and provide space in the balloon for conductive fluid to immerse the electrodes.

In some embodiments, the catheters described herein include additional low-profile elements, such as coplanar electrodes, which further reduce the diameter of the distal end of the catheter. Additionally or alternatively, the catheters may provide an electrical connection to the electrodes by way of a reinforced wire sheath wrapped circumferentially around the catheter shaft. The reinforced wire sheath provides improved kink resistance, torqueability, and pushability to the catheter for more easily maneuvering the device within a patient's vasculature.

FIG. 1 illustrates an exemplary catheter 10 for treating occlusions in blood vessels according to an embodiment of the subject invention. The catheter 10 is advanced into an occlusion in a patient's vasculature, such as the stenotic lesion depicted in FIG. 1, over a guidewire 20 carried in a guidewire sheath. A distal end of the catheter 10 includes a shock wave generator 16 that produces shock waves at a plurality of emitters (e.g., electrode pairs) to break up calcified lesions. As used herein, the plurality of emitters include electrode pairs having first and second electrodes separated by a gap, at which shock waves are formed when a current flows across the gap between the electrodes of the pair (i.e., when a voltage is applied across the first and second electrodes). The electrodes pairs are arranged in a low-profile configuration that reduces the diameter of the distal end of the catheter 10 and permits the treatment of tight, hard-to-cross lesions. In some examples, the shock wave generator 16 includes one or more coplanar electrode pairs, or includes one or more electrodes at least partially recessed into the catheter 10.

A low-profile flexible cap or balloon 18 is sealably attached to the distal end of the catheter 10, forming an annular channel around the shaft 12 of the catheter. The flexible cap or balloon 18 surrounds the shock wave generator 16, such that the shock waves are produced in a closed system defined by the walls of the cap. The cap or balloon 18 is filled with a conductive fluid, such as saline. The conductive fluid allows the acoustic shock waves to propagate from the electrode pairs of the shock wave generator 16 through the walls of the cap or balloon 18 and then into the target lesion. In some embodiments, the conductive fluid may also contain an x-ray contrast agent to permit fluoroscopic viewing of the catheter 10 during IVL treatment. In some embodiments, the cap is rigid and not flexible. In some embodiments, when inflated with conductive fluid, the diameter of the cap expands up to 10-15% maximum.

Further, the catheter 10 also includes a proximal end or handle 22 that remains outside of a patient's vasculature during treatment. The proximal end 22 includes an entry port for receiving the guidewire 20. The proximal end 22 also includes a fluid port 26 for receiving a conductive fluid for inflating and deflating the flexible cap 18 during treatment. An electrical connection port 24 is also located on the proximal end 22 to provide an electrical connection between the distal shock wave generator 16 and an external pulsed high voltage source 28, such as the intravascular lithotripsy (IVL) generator shown in FIG. 1. In some embodiments, the handle is a Y-adaptor. In some embodiments, strain relief is provided at junction of the handle.

The catheter 10 also includes a flexible shaft 12 that extends from the proximal handle 22 to the distal end of the catheter. The shaft 12 comprises an inner member that provides various internal conduits connecting elements at the distal end with the handle 22 of the catheter. As described below, the inner member includes a guidewire lumen for receiving the guidewire 20. The inner member also defines a number of further lumens extending longitudinally through the shaft 12. For instance, one or more wire lumens can be included for carrying conductive wires that electrically connect the pulsed voltage source 28 with electrodes of the distal shock wave generator 16. In some embodiments, one or more fluid lumens (e.g., a fluid inlet lumen and a fluid outlet lumen) are provided in the inner member for carrying conductive fluid from the fluid port 26 into the cap or balloon 18. In some embodiment, the same lumen can be used to carry both wire(s) and conductive fluid.

Optionally, the flexible shaft 12 includes a reinforced wire sheath wrapped circumferentially around the inner member. The reinforced wire sheath provides mechanical support to the flexible shaft 12 to facilitate torqueing, pushing, and maneuvering of the catheter 10 through a patient's blood vessel. In some embodiments, a tubular outer jacket or a plastic liner covers the guidewire sheath and the reinforced wire sheath to provide a barrier between active elements of the catheter 10 and the in situ environment. In some embodiments, additional proximal reinforcement can be applied for added push-ability and torque-ability (by means of additional plastic, metal, or other potential strengthening components).

Figure 2A:
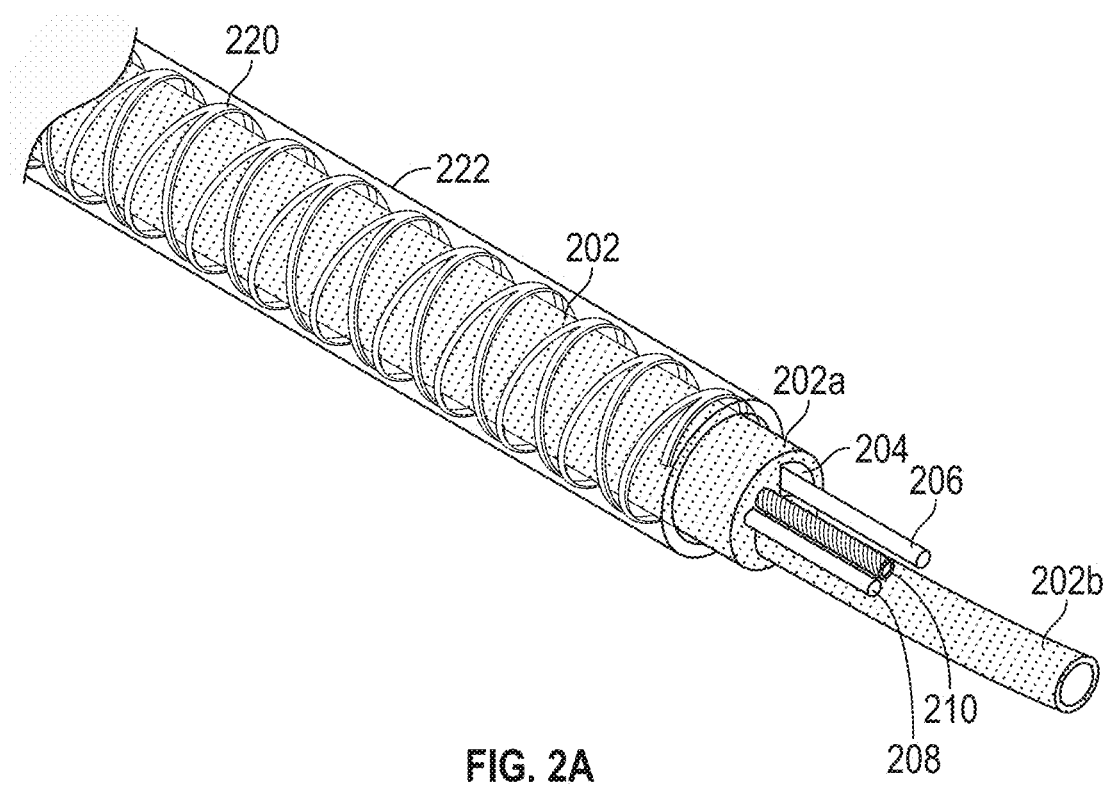
FIG. 2A is an illustration of components at the distal end of a catheter, in accordance with some embodiments of the subject invention.

FIG. 2A is an illustration of components at the distal end of a catheter (e.g., catheter 10), in accordance with some embodiments of the subject invention. The catheter comprises an inner member 202. The inner member 202 comprises a base segment 202a and a low-profile extension segment 202b. Both the base segment 202a and the extension segment 202b are cylindrical, with the diameter of the extension segment 202b smaller than the diameter of the base segment 202a, thus creating a low-profile distal end.

The low-profile extension segment 202b comprises a lumen for accommodating a guidewire (e.g., guidewire 20). The base segment 202a carries two wires 206 and 208. Wires 206 and 208 are insulated wires (e.g., polyimide-insulated copper wires) with conductive distal ends. In some embodiments, the insulating layer of the distal ends of the wires are cut to expose the inner conductive cores of the wires. The two wires, together with a conductive sheath, form two electrode pairs for generating shockwaves, as described herein.

The location, size, and shape of the removed portion of the insulation may vary to control the location, direction, and/or magnitude of the shock wave. In some embodiments, flat wires rather than round wires are used to further reduce the crossing profile of the electrode assembly.

The inner member 202 further provides an inlet for conductive fluid. In the depicted example in FIG. 2A, the base segment accommodates a tubing 210 as an inlet flush port for introducing conductive fluid to the distal end of the catheter. The tubing 210 can be a polyimide tubing. In the depicted example, the distal portion of the tubing 210 extrudes out of the base segment. In some embodiments, a mandrel can be placed in the lumen instead of the tubing 210 as an inlet port.

The inner member 202 further provides an outlet for conductive fluid. In the depicted example in FIG. 2A, the base segment comprises an outlet lumen 204 as an outlet flush port for carrying conductive fluid away from the distal end of the catheter. The lumen 204 has two functions—in addition to being the outlet flush port, the lumen 204 also accommodates wire 206 of the electrode assembly, thereby saving space and further reducing the profile of the catheter at the distal end.

Surrounding the inner member 202 is a tubular reinforced wire sheath 220 formed from at least one reinforced wire material such as metal or plastic. The wire material can braided, coiled, or both at varying pitches. The reinforced wire sheath 220 may also provide favorable mechanical properties to the shaft of the catheter. For instance, the material composition of the reinforced wire sheath 220 could provide increased torqueability, pushability, or enhanced rigidity to the catheter shaft to facilitate maneuvering the catheter through a patient's vasculature. The material of the wire sheath 220 can be radiopaque to facilitate visual tracking of the catheter.

Figure 2B:
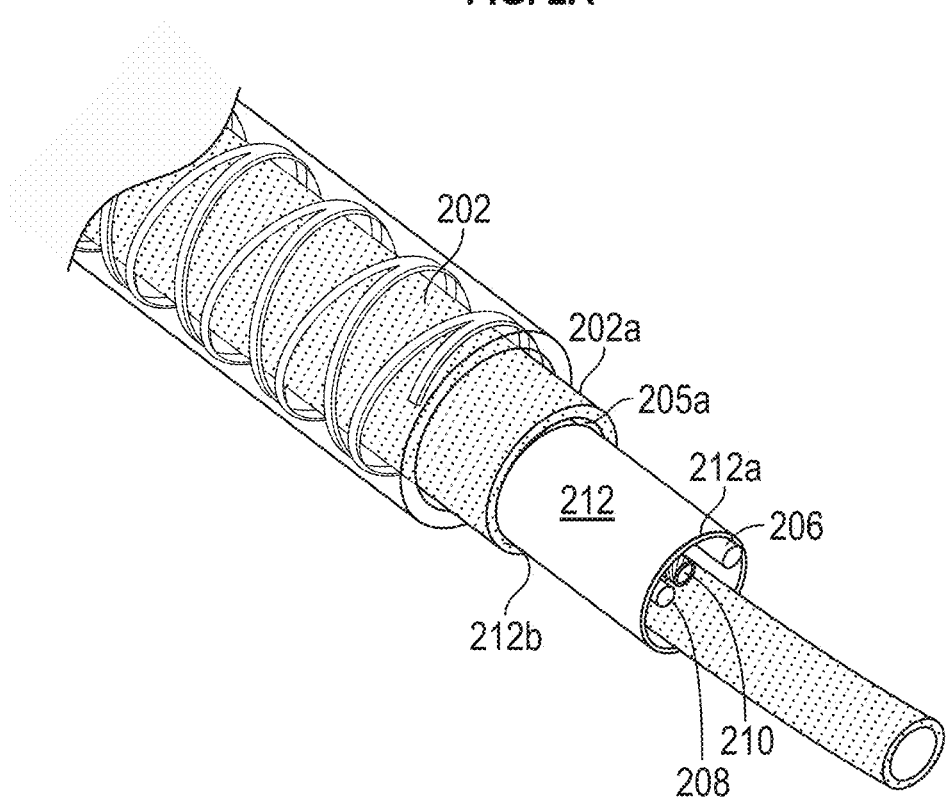
FIG. 2B is an illustration of components at the distal end of the catheter, in accordance with some embodiments of the subject invention.

The reinforced sheath 220 can be laminated with a plastic liner 222. The plastic liner can be of varying materials or hardness to allow for improved mechanical properties such as pushability and torqueability. The sheath 220 and/or the plastic liner 222 may be flattened to reduce the profile of the catheter and allow the catheter to more easily fit into tightly occluded vessels. As shown in FIG. 2B, the reinforced sheath 220 and the plastic liner 222 do not extend to the distal end of the base segment 202a; thus, the distal segment of the base segment 202a is exposed.

With reference to FIG. 2B, a conductive sheath 212 is positioned around the wires 206 and 208 and the flush port tubing 210. The outer diameter of the conductive sheath 212 is smaller than that of the base segment 202a such that the proximal edge 212b of the conductive sheath can lean against the distal surface of the base segment 202a. In some embodiments, adhesive or thermally bonded plastic can be used to hold the wires, the conductive sheath, and flush tubing 210 in place. In some embodiments, the tubing 210 is optional.

The two wires 206 and 208, together with the conductive sheath 212, form an electrode assembly. The electrode assembly comprises two electrode pairs as described in assignee's prior filing U.S. Pub. No. 2019/0150960. For example, the first electrode pair is formed by a conductive portion of the wire 206 (i.e., a first electrode) and a portion of the distal ring edge of the conductive sheath 212 (i.e., a second electrode). The second electrode pair is formed by a portion of the distal ring edge of the conductive sheath 212 (i.e., a third electrode) and a conductive portion of the wire 206 (i.e., a fourth electrode).

The distal end of each wire and the conductive sheath are spaced apart to define a gap between the two electrodes of an electrode pair. The spacing of the gap can be controlled to generate reproducible electrical arcs in the conductive fluid between the electrodes. The spacing of the electrodes may be modified to produce shock waves having a desired magnitude for a given voltage and current output from a pulsed voltage source. The distal ends of the wires 206 and 208 may or may not extrude out of the distal edge of the conductive sheath. The wires 206 and 208 may shorten over time, thus changing the location of the distal ends of the wires relative to the conductive sheath.

The electrode assembly is formed around the low-profile extension segment 202b of the inner member and thus has a low-profile configuration to reduce the diameter of the distal end of the catheter. The first electrode pair and the second electrode pair are located approximately 120 degrees apart circumferentially around the inner member. The electrodes of each pair are spaced apart to define gaps where current can flow to produce shock waves in the conductive fluid inside the flexible cap.

The relative positioning of the conductive sheath 212 at the distal end of the base segment 202a can be configured to control the flow of the conductive fluid. In the depicted example, the conductive sheath does not completely obstruct the outlet lumen 204. Rather, at least a portion of the outlet lumen (i.e., crack 205) is unobstructed outside the outer diameter of the conductive sheath 212. Accordingly, the conductive fluid can be introduced into the conductive sheath 212 via the inlet tubing 210, flushed out of the conductive sheath 212 at its distal end, then flow around the outside of the conductive sheath 212, and finally exit via the outlet lumen 204 (e.g., via crack 205). This way, the inlet tubing 210 and outlet lumen 204 are positioned to maximize fluid flow across the electrode pairs, such that fluid flowed through the distal end of the catheter via the inlet and outlet flows across at least one of the electrode pairs.

The return path of the conductive fluid outside/around the conductive sheath 212 can be maintained in a number of ways. In some embodiments, the conductive sheath 212 can be flattened or oval shaped to allow a larger portion of the outlet lumen 204 (e.g., crack 205) to be accessible outside the conductive sheath. In some embodiments, the conductive sheath 212 can be offset from the central axis of the base segment 202a. In some embodiments, the portion of the outlet lumen 204 inside the conductive sheath 212 can be sealed off such that the conductive fluid only enters via inlet tubing 210 and exits via the outside portion of the outlet lumen 204 (e.g., crack 205).

In alternative embodiments, the conductive sheath 212 can be positioned at the distal end of the base segment 202a such that the outlet lumen 204 is completely within the conductive sheath. Thus, the conductive fluid exits via the outlet lumen 204 within the conductive sheath 212. In still other embodiments, the outlet lumen 204 is partially inside and partially outside the conductive sheath 212 such that the conductive fluid can exit via the outlet lumen 204 either inside or outside the conductive sheath.

In some embodiments, the conductive sheath 212 is formed at least partially from a radiopaque material such platinum, iridium, or stainless steel for creating lithotripsy and to permit fluoroscopic viewing of the catheter during use.

Figure 2C:
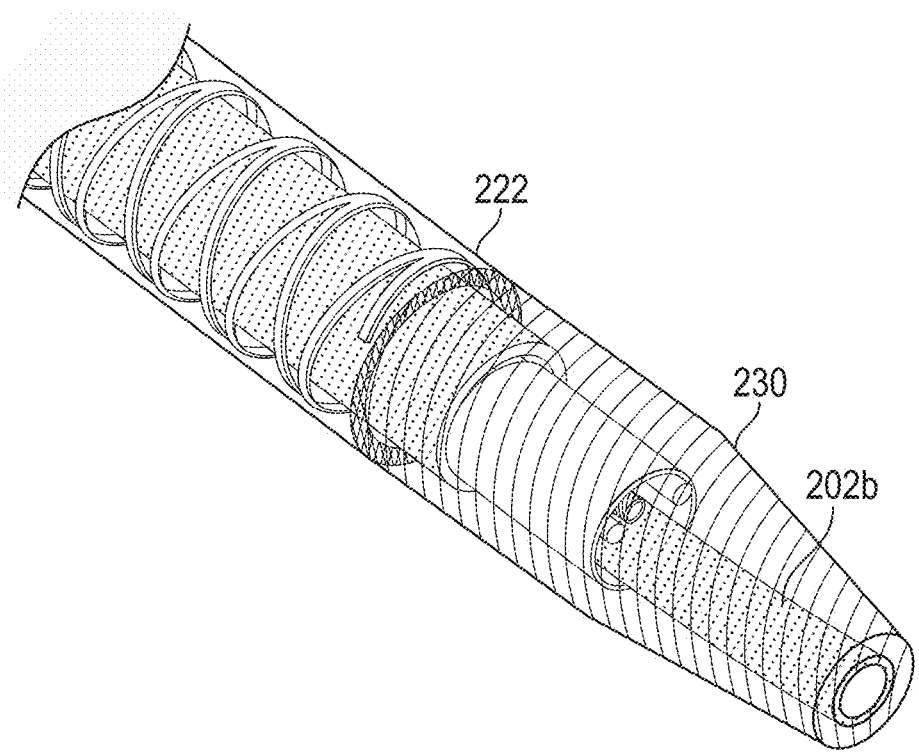
FIG. 2C is an illustration of components at the distal end of the catheter, in accordance with some embodiments of the subject invention.
Figure 2D:
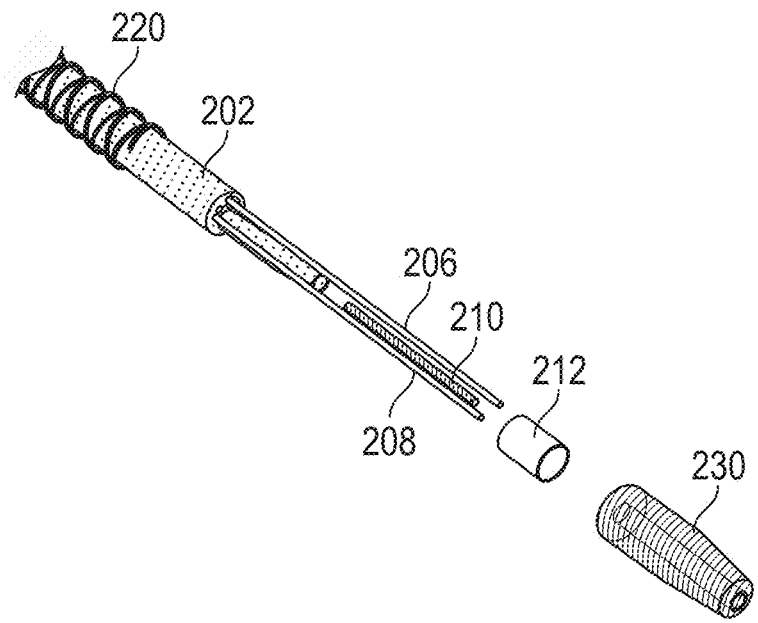
FIG. 2D is an illustration of an exploded perspective view of the distal section of the catheter, in accordance with some embodiments of the subject invention.

Turning to FIG. 2C and FIG. 2D, the distal end of the catheter comprises a no-fold cap 230. The no-fold cap is attached over the distal end of the catheter to close the flush path and encapsulate the emitter assembly. As depicted, the proximal edge of the cap is coupled to the distal edge of the plastic liner 222 to form a closed annular channel around the distal end of the catheter. When conductive fluid is introduced to the distal end of the catheter, the conductive fluid can flow through the emitter assembly and exit via the outlet port. The space between the inner member and the plastic liner can be sealed off from the distal portion of the catheter such that the conductive fluid does not come into contact with the wire sheath 222.

Further, the distal end of the cap can be coupled to the distal end of the extension segment 202b to form a closed space to prevent the conductive fluid from leaking at the distal end. The lumen defined by the extension segment 202b is unobstructed by the cap to allow a guidewire to pass through. The cap 230 can be thermally or adhesively bonded in place.

The cap 230 is a "no-fold" cap because it does not contain material that needs to be folded before insertion into the cardiovascular system. Instead, the cap comprises a piece of extruded tubing (e.g., extruded polymer tubing) stretched and modified to the desired shape and bonded at the distal end of the catheter. Such a cap can be expanded a relatively small amount (e.g., up to 10-15% maximum) sufficient to immerse the electrodes in a conductive fluid before generating shock waves at the electrodes to treat an occlusion. To maintain its low profile shape, the cap is preferably formed of a material (e.g., semi-compliant polymer) such that the cap can be minimally inflated during treatment of an occlusion, and then returns to a low profile state when deflated after treatment. Alternatively, a low-profile balloon can be used. Additional details of the low-profile cap and balloon can be found in U.S. application Ser. No. 17/021,905, which is incorporated herein by reference.

Thus, the cap 230 maintains a very low profile both in expanded and unexpanded state. In some embodiments, the cap 230's profile is lower than 1.5 mm. The extremely low profile of the cap 230 allows the distal end of the catheter to access tightly occluded regions of vasculature. When the cap is inflated with conductive fluid, the cap expands to provide additional space between the inner surface of the cap and the electrode pairs. In some examples, the outer diameter of the extension segment 202b of the inner member is approximately 0.019 to 0.02 inches and the inner diameter of the inflated cap is less than 1.5 mm, providing a space between the inner member and the inner surface of the cap. The space ensures that the electrode pairs are immersed in conductive fluid during shock wave generation and that the inner surface of the cap is sufficiently far from the electrode pairs that the cap material is not damaged by the shock waves. In some embodiments, the diameter of the cap is between 0.75 mm and 1.5 mm.

In some embodiments, the distal end of the catheter can have an atraumatic profile. The atraumatic profile can be the addition of a soft atraumatic tip (not depicted) via adhesive or thermal means. In some embodiments, the soft tip tapers toward the distal tip of the catheter. The soft tip can be formed from a polymer or any other suitable biocompatible material. In a preferred embodiment, the tip is formed at least partially from a radiopaque material such as platinum, iridium, or stainless steel to permit fluoroscopic viewing of the catheter during use. Providing a soft tip may prevent physical damage to blood vessel walls while facilitating contact with and entry into tight lesions in the vasculature.

The operation of the catheter is now described with reference to FIGS. 1-2C. The catheter 10 can be used to treat occlusions in vasculature, for example, stenotic lesions, calcified portions of an artery, or some other occlusion in a blood vessel. With reference to FIG. 1, in operation, a physician advances the guidewire 20 from an entry site on a patient (e.g., an artery in the groin area of the leg) to the target region of a vessel (e.g., a region having an occlusion that needs to be broken up). The catheter 10 is then advanced over the guidewire 20 to the target region of the vessel. In some examples, the flexible cap 18 sealed to the distal end is a no-fold cap having a low profile, such that the cap can be freely advanced through the vasculature. During the positioning stage of treatment, a guide catheter or wire sheath may be used to aid the entry and maneuvering of the catheter 10 within the vasculature. The wire sheath provides tubular linear support to the catheter shaft 12 during pushing, crossing, and placement of the catheter 10. The in situ location of the distal end of the catheter 10 may be determined by x-ray imaging and/or fluoroscopy.

The distal end of the catheter 10 is advanced as far as possible inside the tight lesion. The flexible cap 18 is then minimally inflated by a conductive fluid (e.g., saline and/or saline mixed with an image contrast agent) introduced via the fluid port 26, allowing conductive fluid to expand the cap so that the outer surface of the cap contacts the target lesion. The cap is inflated to IVL pressure, which is between approximately one atmosphere and approximately six atmospheres. The diameter of the flexible cap in an inflated state may be up to 10-15% greater than the diameter of the flexible cap in a deflated state. However, in some examples the diameter of the cap in an inflated state is even less than 10% greater than the diameter of the cap in a deflated state.

A voltage pulse is then applied by the pulsed high voltage source 28 across one or more electrode pairs (i.e., emitters of the shockwave generator 16). With reference to FIG. 2B, in operation, a physician may trigger the power supply which will supply current simultaneously across the wires 206 and 208. In such an example, current will flow from the voltage source, down the wire 206, across the first gap between the insulation removed distal portion of the wire 206 and the edge of the conductive sheath 212, creating a plasma arc that generates a shock wave at the first electrode pair. The current also flows across the conductive sheath 212 and across a second gap between the edge of the conductive sheath 212 and the insulation removed distal portion of the wire 208, creating another plasma arc that generates a shock wave at the second electrode pair. The current return path is along wire 208 to reach the negative lead or ground.

Each pulse initially ionizes the conducive fluid in the low-profile cap 230 (FIG. 2C) to create small gas bubbles at the distal end of the catheter. Fluid can be continuously flushed through the cap via the inlet lumen and outlet lumen during treatment at a constant rate to clear the bubbles and debris from the electrodes. The fluid flow rate may be controlled throughout treatment, but is generally in the range of approximately 1 ml/min to approximately 3 ml/min. At some point, a plasma arc forms across the electrode pairs, creating a low impedance path where current flows freely. The heat from the plasma arc heats the conductive fluid creating a rapidly expanding vapor bubble. The expansion of the vapor bubble creates a shock wave that is conducted through the fluid, through walls of the low-profile cap, and into an occlusion where the energy breaks up the hardened lesion.

For treatment of an occlusion in a blood vessel, the voltage pulse applied by the voltage pulse generator 28 is typically in the range of approximately 2000 volts to approximately 3000 volts and preferably between 2300 and 3000 volts. The repetition rate or frequency of the applied voltage pulses may be between approximately 1 Hz and approximately 10 Hz. However, the preferred voltage and repetition rate may vary depending on, e.g., the size of the lesion, the extent of calcification, the size of the blood vessel, the attributes of the patient, or the stage of treatment. For instance, a physician may start with low energy shock waves and increase the energy as needed during the procedure. The magnitude of the shock waves can be controlled by controlling the voltage, current, duration, and repetition rate of the pulsed voltage from the pulsed voltage source 28. More information about the physics of shock wave generation and their control can be found in U.S. Pat. Nos. 8,956,371; 8,728,091; 9,522,012; and 10,226,265, each of which is incorporated by reference.

During an IVL treatment, one or more cycles of shock waves can be applied to create a more compliant vessel. For example, once the stenosis has been softened sufficiently by a first cycle of shock waves, the low-profile cap 230 can be deflated and the distal end of the catheter can be advanced further into the occlusion. The flexible cap 230 is then re-inflated and another cycle of shock waves can be applied. Further advancement of the cap 230 can be attempted after the completion of successive cycles.

In some embodiments, the catheter can be used to treat a total occlusion in a blood vessel, for instance, a coronary total occlusion (CTO). When treating a total occlusion, the guidewire is advanced at least partially into the stenotic lesion. The catheter is then advanced through the patient's vasculature over the guidewire and at least partially into the lesion. The low-profile cap is then inflated with a conductive fluid until the cap gently contacts the lesion. Voltage pulses are then supplied by a pulsed voltage source to electrode pairs at the tip of the catheter to generate shock waves that break up or loosen the lesion. The guidewire and the catheter can then be advanced further into the lesion and the shock wave treatment can be repeated until the total occlusion is cleared or until the diameter of the vessel permits the placement of a larger more conventional angioplasty device.

In some embodiments, the catheter can be used in a small vessel that is partially blocked by a stenotic lesion. In this situation, the guidewire can be advanced much further into the lesion and, in some cases, all the way through the lesion. After positioning the guidewire, the catheter is advanced through the lesion in incremental stages. At each stage, the low-profile cap is inflated and shock waves are generated to break up the occlusion and increase the diameter of the blood vessel. As noted above, once the diameter of the vessel is sufficiently large, a larger-diameter catheter may be advanced through the vessel to complete the treatment.

The progress of the procedure may be monitored by x-ray and/or fluoroscopy. Shock wave cycles can be repeated until the occlusion has been cleared, or until a channel is formed in the lesion having a diameter sufficient to receive a second treatment device having a larger profile. For example, the enlarged channel can receive a different catheter having a more conventional angioplasty balloon or differently oriented shock wave sources. Catheters of this type are described in U.S. Pat. No. 8,747,416 and U.S. Publication No. 2019/0150960, cited above. Once the lesion has been sufficiently treated, the flexible cap 18 may be inflated further, then deflated, and catheter 10 and guidewire 20 can be withdrawn from the patient.

Figure 3A:
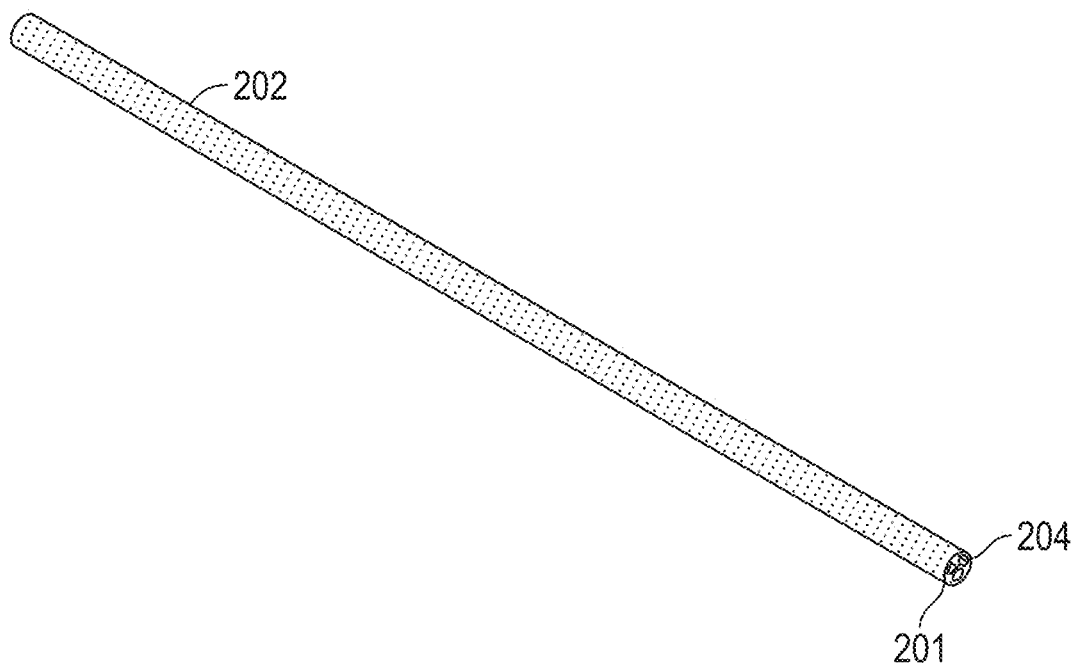
FIG. 3A is an illustration of a step in an exemplary process of manufacturing a catheter, in accordance with some embodiments of the subject invention.

FIGS. 3A-E illustrate steps in an exemplary process of manufacturing a catheter, in accordance with some embodiments of the subject invention. FIG. 3A depicts a tubular inner member 202 comprising 3 lumens (i.e., a tri-lumen shape). In some embodiments, polyimide or etched PTFE tubing can be used in one or more of the lumens. For example, the lumen 201 (i.e., the lumen carrying the fluid inlet port) and the lumen 204 (i.e., the lumen acting as the fluid outlet) each can include polyimide lining to prevent any cross-talking between the inflow and the outflow of the conductive fluid in the catheter.

Figure 3B:
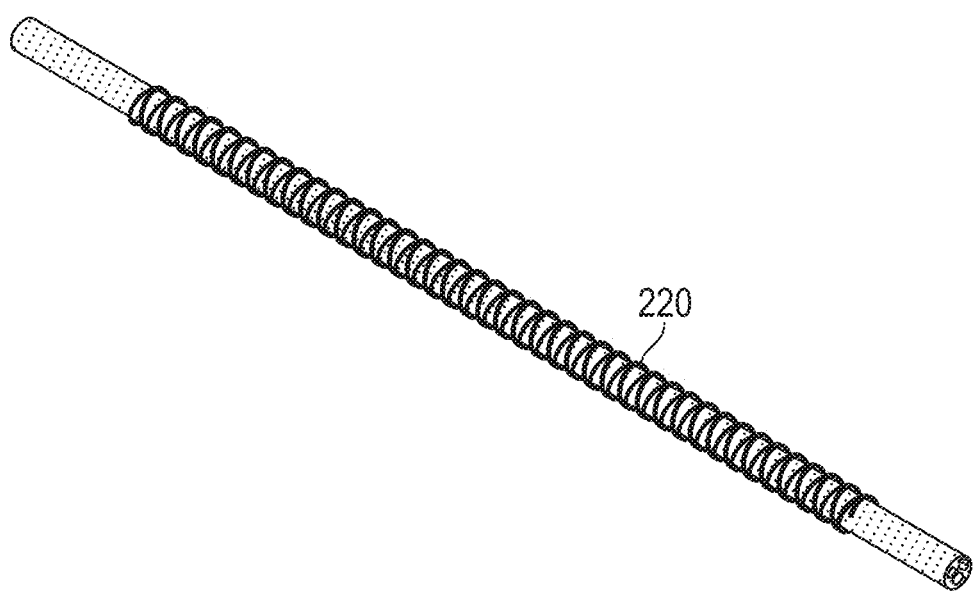
FIG. 3B is an illustration of a step in an exemplary process of manufacturing the catheter, in accordance with some embodiments of the subject invention.

With reference to FIG. 3B, a tubular reinforced wire sheath 220 is applied over the inner member. In the depicted example, the wire sheath 220 comprises reinforced braided wire structure threaded over inner member. The proximal and distal segments of the inner member are not over-braided. The wire material can braided, coiled, or both at varying pitches and sizes. The reinforced wire sheath 230 may also provide favorable mechanical properties to the shaft of the catheter. For instance, the material composition of the reinforced wire sheath 220 could provide increased torqueability, pushability, or enhanced rigidity to the catheter shaft to facilitate maneuvering the catheter through a patient's vasculature.

Figure 3C:
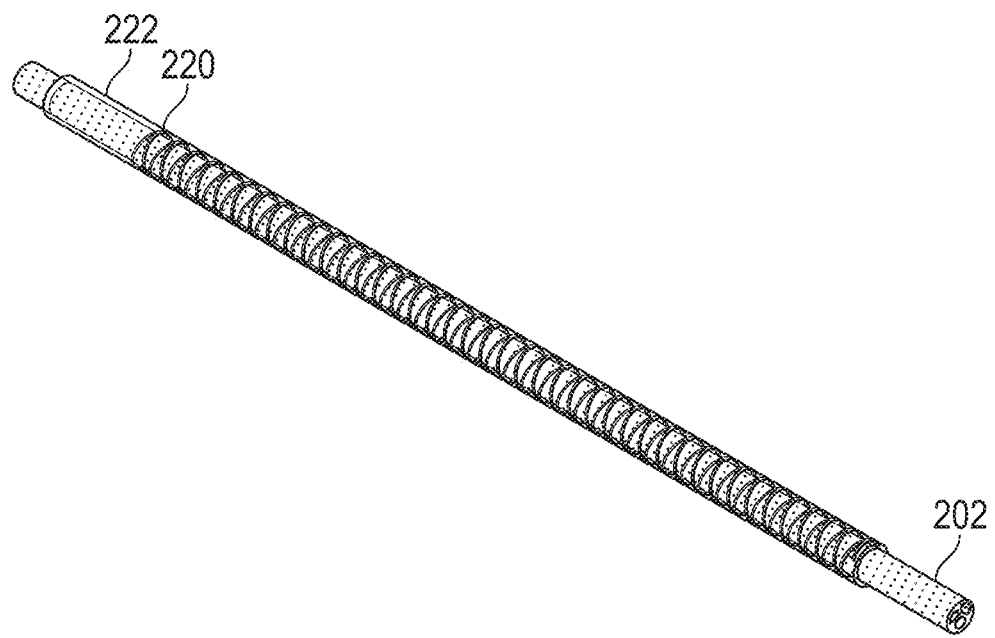
FIG. 3C is an illustration of a step in an exemplary process of manufacturing the catheter, in accordance with some embodiments of the subject invention.

With reference to FIG. 3C, the reinforced sheath 220 can be encompassed with a plastic liner 222 to create one assembly. The plastic liner can be of varying materials or hardness to allow for improved mechanical properties such as pushability and torqueability. As shown in FIG. 3C, the reinforced sheath 220 and the plastic liner 222 do not extend to the distal end of the inner member 202.

Figure 3D:
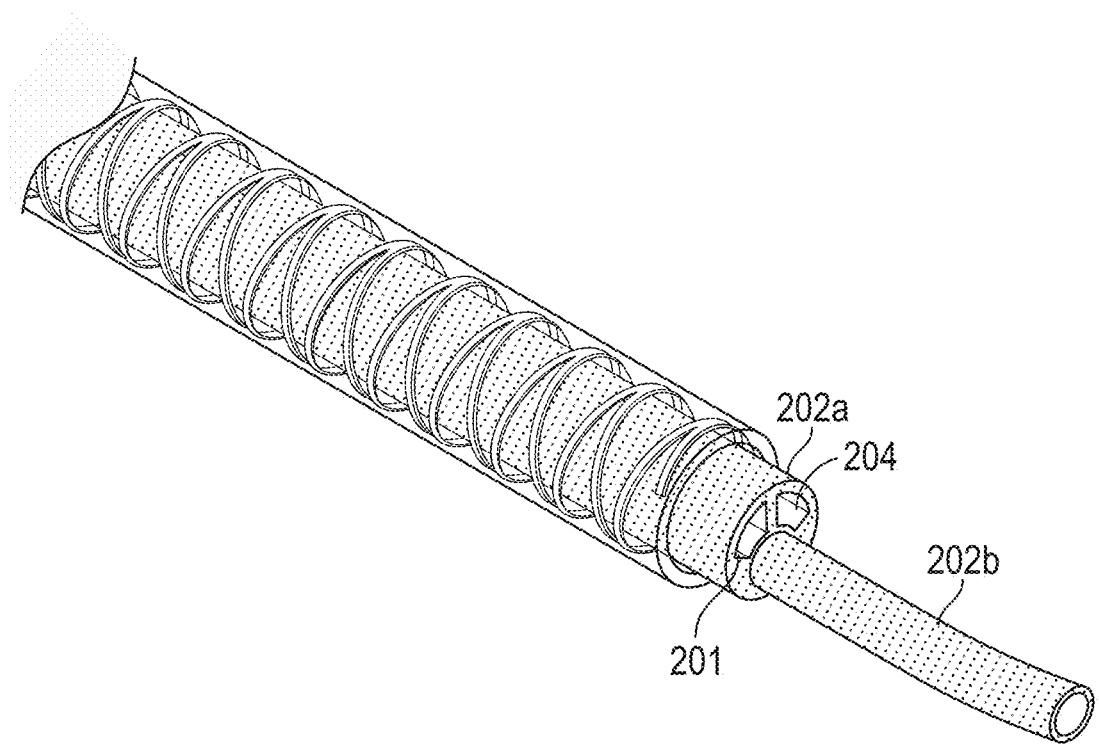
FIG. 3D is an illustration of a step in an exemplary process of manufacturing the catheter, in accordance with some embodiments of the subject invention.

With reference to FIG. 3D, the distal end of the inner member is trimmed to form a base segment 202a and an extension segment 202b. As shown, at the extension segment 202b, only one lumen remains for carrying a guidewire. The reduced outer diameter of the distal segment of the inner member is used to house an emitter assembly as shown in FIG. 2A-C.

Figure 3E:
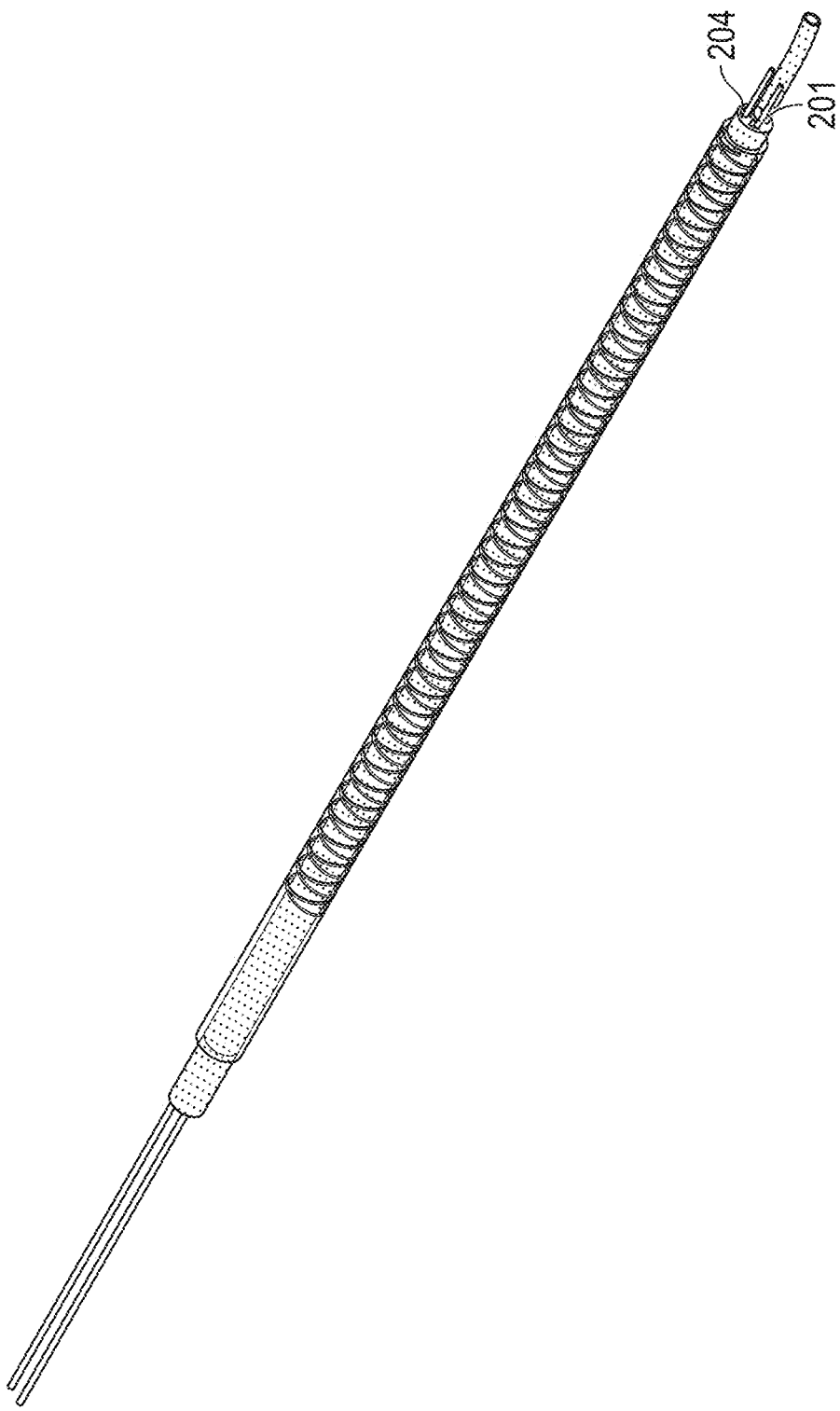
FIG. 3E is an illustration of a step in an exemplary process of manufacturing the catheter, in accordance with some embodiments of the subject invention.

With reference to FIG. 3E, two wires of the emitter assembly are loaded down the lumens 201 and 204. As discussed above, the two lumens each can include polyimide lining to insulate the lumens and prevent any fluid connection between the two lumen (which may cause short-circuit). In some embodiments, the inner member may comprise additional lumens in the base segment 202a for accommodating additional emitter assemblies. Additionally or alternatively, multiple wires (e.g., from multiple emitter assemblies) can be accommodated in one lumen in the inner member.

After the wires are loaded, a tubing (e.g., a tubing 210 in FIG. 2A) is inserted in lumen 201 as an inlet flush port for introducing conductive fluid to the distal end of the catheter. The lumen 201 is sealed with adhesive or thermally bonded, as shown in FIG. 2A. Alternatively, a mandrel can be placed in lumen 201 instead of tubing and then sealed with adhesive or thermally bonded.

In some examples, each wire is a polyimide insulated copper wire having a diameter between approximately 0.003 inches and approximately 0.007 inches. The wires may be flattened to reduce the profile of the catheter, with the flattened wires having a cross-section that is approximately 0.003 inches thick and approximately 0.010 inches wide. Further, lumens in the inner member may have any desired shape. The location, size, and shape of any of the lumens can be modified to reduce the profile of the catheter or to provide some other benefit. Further, the various lumens may be combined (e.g. by providing two or more insulated wires in the same lumen) or eliminated without departing from the scope of the present invention.

Figure 4A:
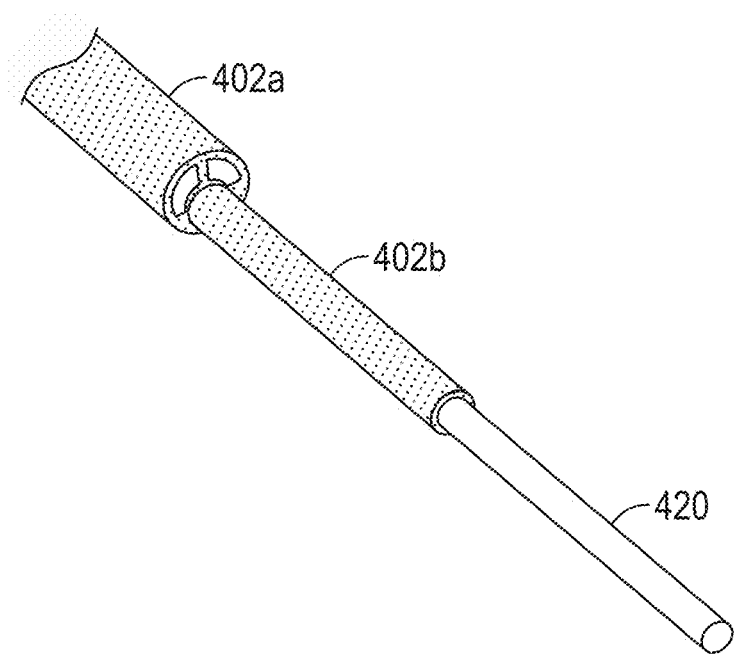
FIG. 4A is an illustration of components at the distal end of another exemplary catheter, in accordance with some embodiments of the subject invention.
Figure 4B:
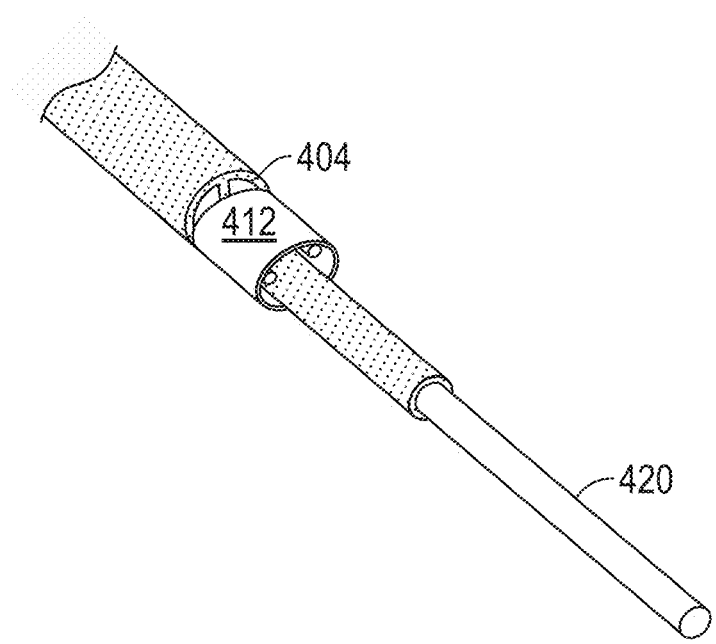
FIG. 4B is an illustration of components at the distal end of the catheter, in accordance with some embodiments of the subject invention.
Figure 4C:
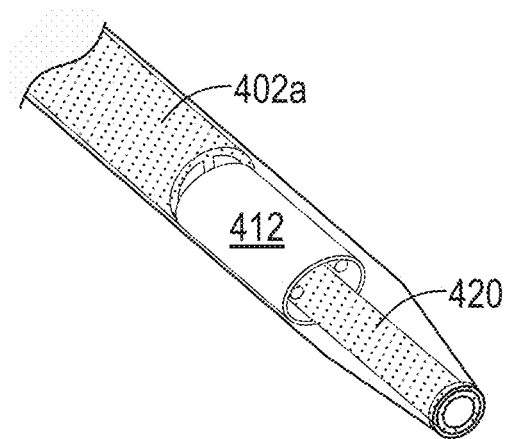
FIG. 4C is an illustration of components at the distal end of the catheter, in accordance with some embodiments of the subject invention.

FIGS. 4A-C illustrate the distal end of another exemplary catheter, in accordance with some embodiments of the subject invention. The catheter comprises an oval-shaped conductive sheath to achieve a lower-profile and/or provide a larger portion of the fluid outlet port to be accessible outside the conductive sheath, as described below.

With reference to FIG. 4A, the catheter comprises an inner member 402 comprising a base segment 402a and an extension segment 402b. The inner member can be manufactured in a similar process as described above with reference to FIGS. 2A-3E, and can operate in a similar manner. The extension segment 402b carries a mandrel 420, which acts as the guidewire lumen.

With reference to FIG. 4B, an emitter assembly, which comprises two wires and a conductive sheath 412, is installed around the low-profile extension segment 402b of the inner member. In the depicted example, the two wires are spaced circumferentially around the extension segment 402b approximately 150 degrees apart to achieve a lower profile and to generate shock waves more evenly around the catheter. Further, the conductive sheath 412 is oval-shaped or flattened to achieve a lower-profile. Further, the oval shape provides a larger portion of the fluid outlet port 404 to be accessible outside the conductive sheath and allows the conductive fluid to flow over the conductive sheath.

With reference to FIG. 4C, a low-profile cap is attached over the distal end to close the flush path and encapsulate the emitter assembly. The cap can be attached with adhesive or thermally bonded to the inner member. As described above, the most distal tip has an atraumatic profile applied, either by thermal means or the addition of a soft atraumatic tip via adhesive.

In the embodiments depicted in FIG. 2A-4C, the inner member comprises three lumens: a first lumen (e.g., 201 in FIG. 3D) that both accommodates a first wire 208 and serves as an inlet flush port, a second lumen (e.g., 204 in FIG. 3D) that both accommodates a second wire 206 and serves as an outlet flush port, and a third lumen that accommodates a guidewire. However, it should be appreciated that the design of the inner member is not so limited. For example, the inner member can include additional lumens such that separate lumens can be used to accommodate a wire and serve as a flush port.

For example, the inner member can include four lumens: a first lumen that accommodates a wire, a second lumen that serves as a flush port, a third lumen that both accommodates the other wire and serves as the other flush port, and a fourth lumen that accommodates a guidewire. As another example, the inner member can include five lumens: two lumens for accommodating the two wires, two lumens for accommodating the two flush ports, and a fifth lumen for accommodating a guidewire. An exemplary inner member having five lumens is depicted in FIGS. 5A-5B as described in detail below.

Further, in the embodiments depicted in FIGS. 2A-4C, in a lumen that both accommodates a wire and serves as a flush port, there are two configurations. One configuration is illustrated by lumen 204, where the lumen's distal end is not sealed and the entire distal opening serves as the flush port. The second configuration is illustrated by lumen 201 (FIGS. 3D and 2A), where the lumen's distal end is sealed to leave only a relatively small opening that serves as the flush port. In the second configuration, an optional tubing 210 can be attached to the small opening to control the precise position of the port. While the embodiments depicted in FIGS. 2A-4C show an inner member having a lumen of the first configuration and a lumen of the second configuration, it should be appreciated that the design is not so limited. For example, an inner member can have two lumens that are both of the first configuration or both of the second configuration. It should be further appreciated that the choice of configuration(s) can affect the amount and distribution of the shockwaves.

In FIGS. 2A-4C, the extension segment (e.g., 202b) is an integral piece of the inner member and can be formed by trimming the distal end of the inner member as shown in FIGS. 3C-D. However, the low-profile segment can be constructed via other means as described below.

Figure 5A:
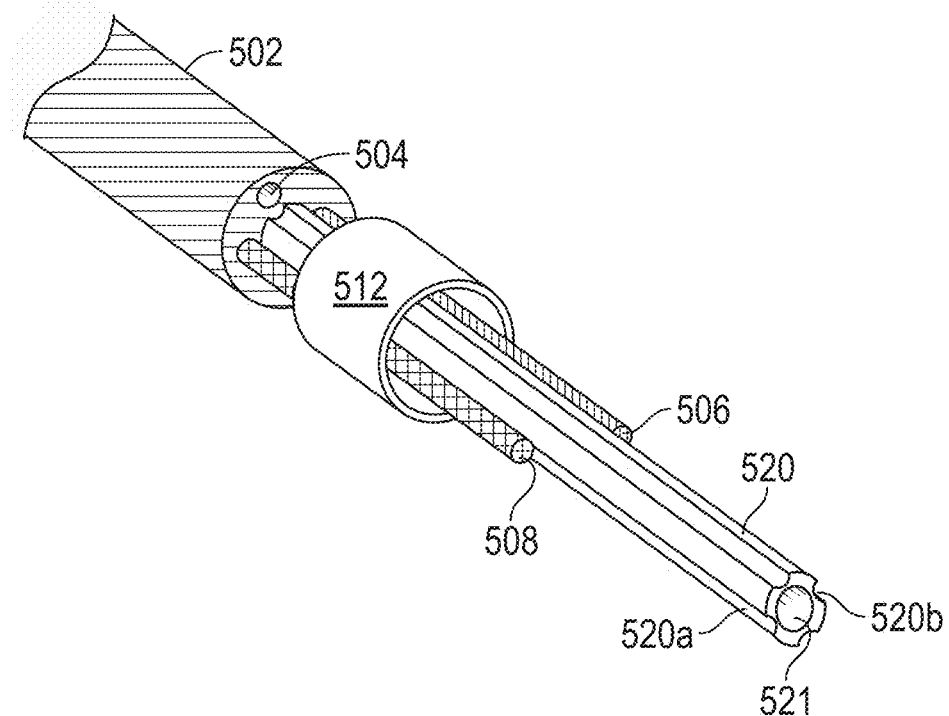
FIG. 5A is an illustration of components at the distal end of another catheter, in accordance with some embodiments of the subject invention.
Figure 5B:
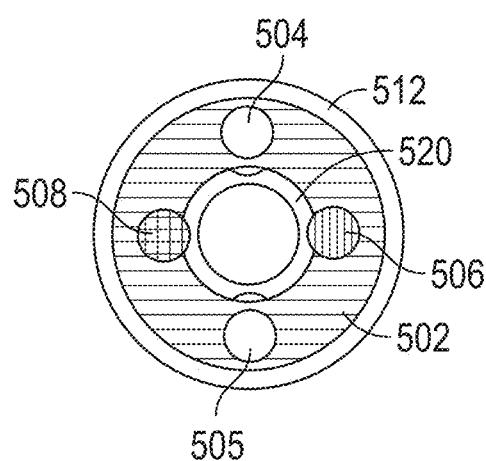
FIG. 5B is a cross-section illustration of components at the distal end of the catheter, in accordance with some embodiments of the subject invention.

FIGS. 5A-B illustrate components of another exemplary catheter, in accordance with some embodiments of the subject invention. In FIGS. 5A-B, a separate guidewire member 520 is attached to the distal end of the inner member 502. Specifically, the proximal end of the guidewire member 520 can be affixed (e.g., glued) to the distal end of the inner member. The lumen 521 in the guidewire member 520 lines up with the central lumen of the inner member 502 such that a guidewire can extend through the inner member and the guidewire member.

In some embodiments, in order to attach the guidewire member 520 to the inner member 502, a small portion of the proximal end of the guidewire member (e.g., 2-3 mm) is inserted into the central lumen of the inner member. Heat can be applied to melt the materials at the location of the insertion to bond the guidewire member to the inner member. In some embodiments, mandrels can be placed in the lumens of the inner member and/or the guidewire member during heating to prevent the lumens from being deformed by the heat.

With reference to FIGS. 5A and 5B, the outer surface of guidewire member 520 includes grooves 520a and 520b. Because the wires 506 and 508 are flexible, the distal portions of the wires can be placed within the grooves to further secure the wires (e.g., via glue) and reduce the distal profile of the catheter. A conductive sheath 512 is wrapped circumferentially around wires and the guidewire member. Lumens 504 and 505 define the two independent flush ports.

While the inner member 502 comprises five lumens (two for accommodating the two wires, two for serving as flush ports, and one for accommodating the guidewire), it can instead comprise three lumens or four lumens as described above.

FIGS. 6A-6D illustrate components of another exemplary catheter in accordance with an embodiment of the subject invention. This embodiment is similar to the embodiment of FIG. 5 with some changes as noted below.

In this embodiment, the inner member 620 is formed from a single extrusion having four channels or flutes 640, 642 (two visible in FIG. 6A) and a guidewire lumen 621. The distal end of the member 620 is necked down to provide a reduced diameter region at the distal end. The more proximal portion of the inner member has a larger diameter and includes the four channels. One polyimide tube 644, 646 (four total) is aligned with each of the four channels. Two of the tubes are used for carrying a wire. One of the tubes provides an inlet for supplying a conductive fluid to the distal tip of the catheter and the fourth tube provides a return path for the fluid. The fourth tube could be connected to a suction source.

Figure 6A:
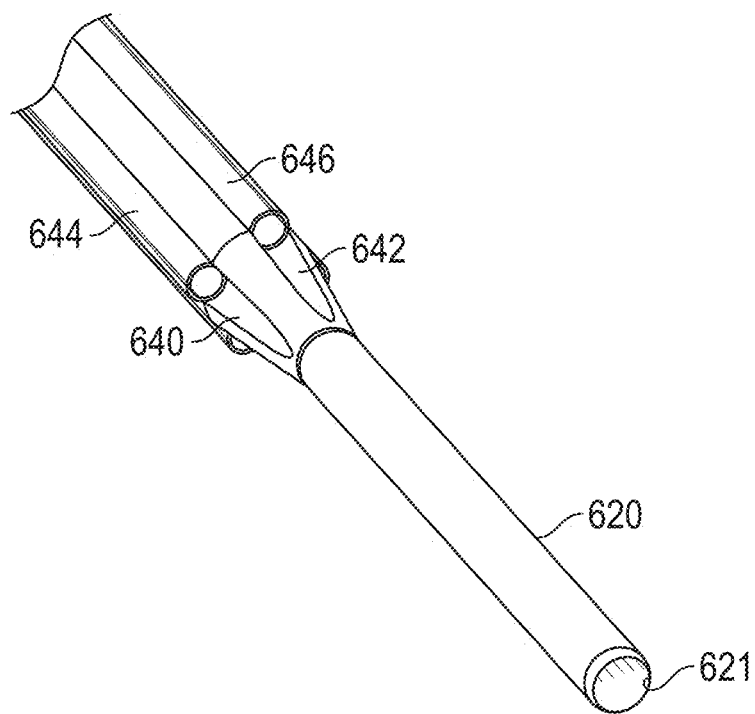
FIG. 6A is an illustration of components at the distal end of another catheter in accordance with an embodiment of the subject invention.
Figure 6B:
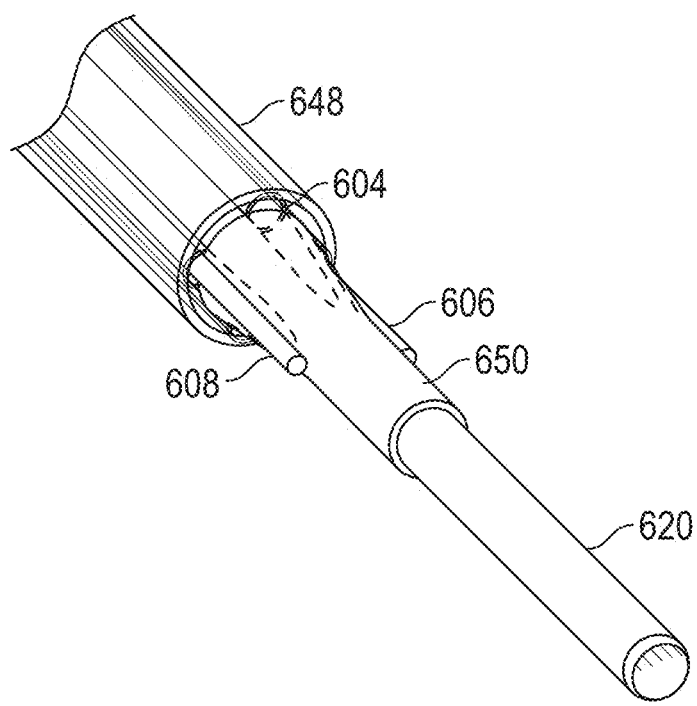
FIG. 6B is an illustration of components at the distal end of the catheter of FIG. 6A in a later stage of manufacture

As seen in FIG. 6B, a jacket 648 surrounds the polyimide tubes. A cylindrical insulating sleeve 650 surrounds a portion of the inner member and can extend to the distal openings in the polyimide tubes. The sleeve 650 can be formed from two pieces including a constant diameter distal potion and a tapered proximal portion. In the alternative, the sleeve may be formed of one piece as shown. FIG. 6B also shows two wires 606 and 608, each extending out of a tube and along a portion of the insulating sleeve.

Figure 6C:
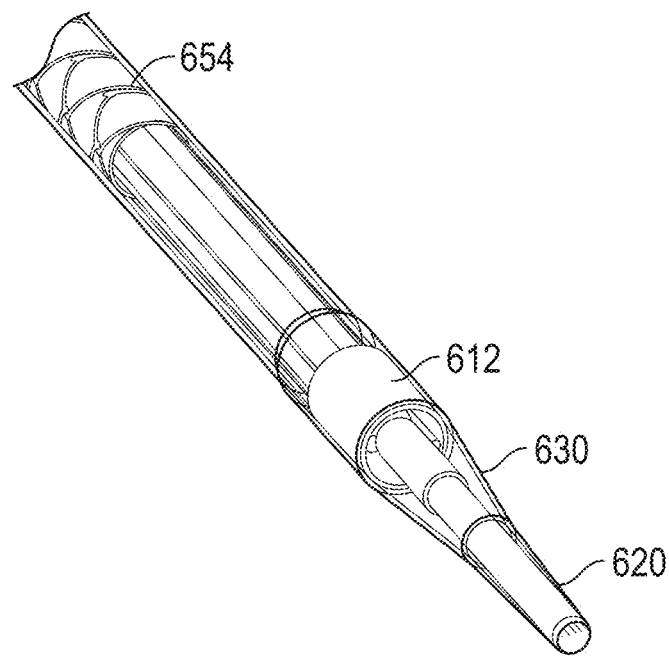
FIG. 6C is an illustration of components at the distal end of the catheter of FIG. 6B in a later stage of manufacture.

A more complete assembly appears in FIG. 6C and includes a cylindrical conductive sheath 612 surrounding the tips of wires 606 and 608 to define two electrode pairs. When a voltage is applied to the proximal ends of wires 606 and 608, current will travel down wire 606, jump the gap between the insulation removed distal end of the wire across to the sheath, then travel around the sheath and jump the gap to the insulation removed distal end of wire 608 where it will return to ground. Shock waves are generated at both gaps as discussed in detail above.

As seen in FIG. 6C, a flexible cap 630 is mounted on the distal end of the catheter. The structure of a minimally expanding cap is discussed above. As in the other embodiments, the more proximal portion of the catheter can include a sheath 654 defined by a reinforced wire braid.

Figure 6D:
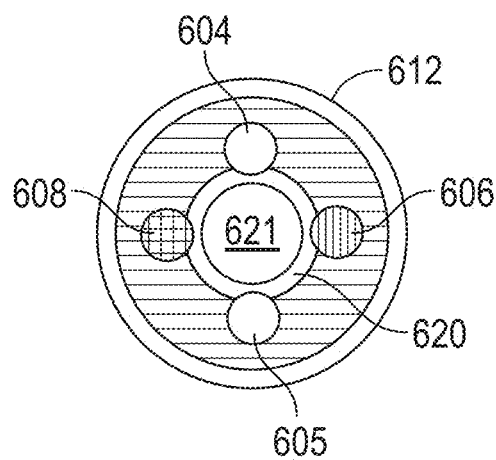
FIG. 6D is a cross-sectional view of some of the components shown in FIG. 6C.

FIG. 6D is a cross section that shows the inner member 620 defining the guidewire sheath 621. Wires 606 and 608 fit within their own tubes. As noted above, tube 604 provides an inlet for conductive fluid and tube 605 can provide a return path for removing fluid. In this embodiment, the wires and the fluid inlet and outlet are separated in separate channels along the catheter.

It should be noted that the elements and features of the example catheters illustrated herein may be rearranged, recombined, and modified without departing from the present invention. Further, the subject invention is intended to include catheters having a variety of electrode configurations. For instance, a shock wave generator of an exemplary catheter could include two tongue-and-groove electrode pairs, two dot and circle electrode pairs, or two electrode pairs formed from distal conductive portions of wires and a conductive sheath, or any other desired configuration. Further, the placement and spacing of the electrode pairs can be modified without departing from the subject invention. For instance, the electrode pairs may be spaced circumferentially around the catheter in consistent increments, e.g., 180 degrees apart, 90 degrees apart, or 60 degrees apart to generate shock waves more evenly around the catheter. In some examples, the shock wave generator includes electrode pairs positioned in various groupings spaced longitudinally along the catheter. For example, the shock wave generator could include a plurality of electrode pairs defined by a plurality of conductive sheaths spaced longitudinally along the catheter. In such examples, the pulsed voltage source may be controlled to selectively generate high voltage pulses at either the proximal or distal electrode pairs, e.g., by applying voltage pulses across differing set of wires or other conductors leading to the respective pairs. For example, in a first stage of treatment (i.e., during initial treatment of the tight or totally-occluding lesion), only the distal electrode pairs are activated to generate shock waves. After the tight lesion has been modified and more proximal portions of the cap 18 are able to cross the lesion, the cap is again inflated and more proximal electrode pairs are activated to generate more proximal shock waves.

It will also be understood that the position of the wires and fluid channels may be varied from the illustrated configurations. For example, and considering FIG. 6D, the location of wire 608 and channel 605 could be swapped. In fact, any two tubes can contain wires and any two channels can be used for fluid exchange. Further, the angular spacing of the elements may be adjusted to improve performance.

It will be understood that the foregoing is only illustrative of the principles of the invention, and that various modifications, alterations and combinations can be made by those skilled in the art without departing from the scope and spirit of the invention. Any of the variations of the various shock wave catheters disclosed herein can include features described by any other shock wave catheters or combination of shock wave catheters herein. Furthermore, any of the methods can be used with any of the shock wave devices disclosed. Accordingly, it is not intended that the invention be limited, except as by the appended claims.

The invention claimed is:

1. A catheter for treating occlusions in blood vessels comprising:
    a tubular inner member having a proximal portion with a first diameter and a distal end portion having a second diameter smaller than the first diameter, with the proximal portion of the inner member including four circumferentially positioned flutes, each of the circumferentially positioned flutes receiving one of four tubes,
    a first wire located in a first tube of the four tubes and extending distally beyond the first tube;
    a second wire located in a second tube of the four tubes and extending distally beyond the second tube;
    a third tube of the four tubes connectable to a source of conductive fluid;
    a fourth tube of the four tubes configured to define a return path for the conductive fluid;
    a cylindrical insulation sheath positioned around the distal portion of the inner member and radially inside the distal ends of the first and second wires;
    a cylindrical conductive sheath surrounding the distal ends of the first and second wires and defining two electrode pairs;
    a sheath surrounding the proximal portion of the inner member; and
    a flexible cap surrounding the conductive sheath and a distal tip of the catheter.

2. The catheter of claim 1 wherein the inner member is formed from a single extrusion.

3. The catheter of claim 1 wherein the fourth tube is connectable to a source of suction.

4. The catheter of claim 1 wherein the sheath surrounding the proximal portion of the inner member is a wire braid.

5. The catheter of claim 1 wherein the inner member further includes a central guidewire lumen.

6. The catheter of claim 1, comprising a cylindrical jacket surrounding the first tube, the second tube, the third tube, and the fourth tube.

7. The catheter of claim 1, wherein the cylindrical insulation sheath comprises a constant diameter distal portion and a tapered proximal portion.

8. The catheter of claim 1, wherein the distal end of the first wire is uninsulated and is separated from the cylindrical conductive sheath by a first gap.

9. The catheter of claim 8, wherein the distal end of the second wire is uninsulated and is separated from the cylindrical conductive sheath by a second gap.

10. The catheter of claim 9, wherein when a voltage is applied to the proximal ends of the first wire and the second wire, current jumps the first gap between the uninsulated distal end of the first wire and the cylindrical conductive sheath to generate a first shock wave, and jumps the second gap between the uninsulated distal end of the second wire and the cylindrical conductive sheath to generate a second shock wave.

* * * * *